United States Patent [19]
Drapeau et al.

[11] Patent Number: 5,830,761
[45] Date of Patent: Nov. 3, 1998

[54] MEDIUM AND METHODS FOR CULTURING MAMMALIAN CHO CELLS

[75] Inventors: Denis Drapeau, Salem, N.H.; S. Robert Adamson; Yen-Tung Luan, both of Chelmsford, Mass.; Paul Thoday, Sterling, Mass.

[73] Assignee: Genetics Institute, Inc., Cambridge, Mass.

[21] Appl. No.: 481,774

[22] Filed: Jun. 7, 1995

[51] Int. Cl.⁶ ........................................ C12N 5/00
[52] U.S. Cl. ........................................... 435/404; 435/358
[58] Field of Search .............................. 435/240.3, 358, 435/404

[56] References Cited

U.S. PATENT DOCUMENTS 5,166,322  11/1992  Shaw et al. .

FOREIGN PATENT DOCUMENTS 2195655  10/1989  United Kingdom .
2251249   7/1992  United Kingdom .
WO 90/03430  4/1990  WIPO .

OTHER PUBLICATIONS

Ling et al., Exp. Cell Res. 52:469–489 (1968).

Walters and Gilbert, J. Biol. Chem. 261:13135–13143 (1986).

Bannai et al., J. Biol. Chem. 264:18480–14848 (1989).

*Primary Examiner*—Leon B. Lankford, Jr.
*Attorney, Agent, or Firm*—Steven R. Lazar

[57] ABSTRACT

Cell culture media are provided containing high L-cystine concentration and low L-glutamic acid concentration. The media are useful for recombinant production of proteins using mammalian cell cultures.

16 Claims, No Drawings

MEDIUM AND METHODS FOR CULTURING MAMMALIAN CHO CELLS

FIELD OF THE INVENTION

The present invention relates to cell culture media for production of proteins in mammalian cells. More particularly, the present invention relates to a cell culture medium for production of recombinant human bone morphogenetic proteins (BMPs) in Chinese Hamster Ovary (CHO) cells.

BACKGROUND OF THE INVENTION

Traditional cell culture media contain low or zero concentrations of L-glutamate and L-cystine. For example, DME medium contains no L-glutamic acid and L-cystine at 0.2 mM. Ham's F12 medium contains L-glutamic acid at 0.1 mM and no L-cystine. RPMI-1640 contains L-glutamic acid at 0.14 mM and L-cystine at 0.2 mM.

Some cell culture media contain elevated levels of amino acids. Reported cell culture media include high concentrations of both L-cystine and L-glutamic acid. For example, MBRI 40-01 (Celltech, Ltd., GB patent 2,251,249) includes L-cystine at 1.05 mM and L-glutamic acid at 0.7 mM. AN-162 (Ling et al., *Experimental Cell Research,* 52:469–489 (1968)) includes L-cystine at 0.9 mM and L-glutamic acid at 14.4 mM. Ling also describes AN-54, a medium including 0.3 mM L-cystine and 4.8 mM L-glutamic acid. However, these media were not used for the production of recombinant dimeric proteins, such as BMPs.

The BMPs are a subfamily of dimeric proteins, within the TGF-β superfamily of proteins. The isolation and recombinant production of BMPs has been reported. The BMP proteins include BMP-1, BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in PCT application WO94/26893; BMP-11, disclosed in PCT application WO94/26892, or BMP-12 or BMP-13, disclosed in co-pending patent application, Ser. No. 08/362,670, filed on Dec. 22, 1994. Other proteins in the TGF-β superfamily include Vgr-2, and any of the GDFs, including those described in PCT applications WO94/415965, WO94/15949; WO95/01801; WO95/01802; WO94/21681; WO94/15966; and others, BIP, disclosed in WO94/01557; and MP52, disclosed in PCT application WO93/16099. The disclosures of all of the above applications are hereby incorporated by reference. The present invention may also be useful with heterodimers of the above BMP proteins and TGF-β proteins. Examples of preparation of such heterodimers are described in co-pending patent application WO93/09229, filed on Apr. 7, 1992. The disclosures of all of the above references are incorporated herein by reference.

It is desirable to have available improved cell culture media which can be used to in order to produce recombinant proteins, particularly dimeric proteins such as the above members of the TGF-β superfamily and BMP subfamily of proteins, in mammalian cell cultures.

SUMMARY OF THE INVENTION

The present invention comprises mammalian cell culture media which are useful for the production of recombinant proteins in active covalently bonded dimeric form. In particular, these cell culture media are useful for recombinant production of dimeric proteins, particularly bone morphogenetic proteins, such as recombinant human BMP-2 (rhBMP-2), using mammalian host expression systems. The preferred mammalian hosts are CHO cells.

In one embodiment, the invention comprises compositions useful for culturing mammalian cells, said compositions comprising a high concentration of L-cystine and a low concentration of L-glutamic acid. The concentration of L-cystine is at least about 0.6 mM, preferably at least about 0.9, and most preferably at least about 1.4 mM. The concentration of L-glutamic acid is at or below about 0.5 mM, preferably at or below about 0.2 mM. In the preferred embodiment, the cell culture medium comprises L-cystine at a concentration of at least about 1.4 mM and L-glutamic acid at a concentration of at or below about 0.2 mM. In one specific preferred embodiment, the cell culture medium comprises L-cystine at a concentration of about 1.4 mM and L-glutamic acid at a concentration of about 0.2 mM.

The present invention may be used with mammalian cells, particularly Chinese Hamster Ovary [CHO] Cells. Other cells which may be useful as hosts in the present invention include monkey COS-1 cell line and the mammalian cell CV-1.

In a preferred embodiment, the recombinant protein is a dimeric protein, preferably a member of the TGF-β superfamily of proteins, most preferably a member of the BMP subfamily of proteins. In particular preferred embodiments, the recombinant protein is BMP-2, BMP-4 or BMP-7.

DETAILED DESCRIPTION OF THE INVENTION

For recombinant production of active proteins which are normally found in dimeric proteins, such as the BMPs, it is desirable to be able to predictably and consistently produce high amounts of covalently bonded dimeric protein, which is relatively stable, and to reduce the amount of other isoforms of protein, such as monomer, non-covalently bonded dissociable dimer, and multimeric protein, which are less stable and tend to interconvert when present in the cell culture medium. The inventors have determined that the presence and relative concentrations of the various isoforms represents a complex effect of cysteine and cystine concentrations in the culture medium on interchain disulfide bonding patterns of multimeric protein products.

For example, in the case of rhBMP-2, the inventors have determined that the active rhBMP-2 produced in CHO cell culture is usually present in a covalently bonded dimeric form with one interchain disulfide bond involving Cys360. However, when cystine levels are low and cysteine levels are high, less of the rhBMP-2 is produced as covalently bonded dimer, and more elutes as a species which is believed to represent a dissociable dimer in which each of the Cys360 residues is in an unbonded thiol form (Cys-SH). On the other hand, when cystine levels are high and cysteine levels are low, less of the rhBMP-2 elutes as the covalently bonded dimer, and more elutes as a peak which is believed to represent a dissociable dimer in which each of the Cys360 residues is bonded to a cysteine molecule (i.e., cysteinylated, non-covalently bonded dissociable dimer).

The inventors have largely overcome this problem by providing mammalian cell culture compositions comprising a high concentration of L-cystine and a low concentration of L-glutamic acid. In the present invention, a high concentration of L-cystine is defined as at least about 0.6 mM cystine, and is more preferably at least about 0.9 mM, at least about 1.05 mM or at least about 1.4 mM. The most preferred concentration of L-cystine is about 1.4 mM. In the present invention, a low concentration of glutamic acid is defined as at or below about 0.5mM and most preferably at or below about 0.2 mM. The compositions of the present invention are believed to maintain an appropriate balance between L-cystine and L-cysteine in the culture to promote formation of the covalently bonded dimer. This balance is influenced by the concentration of L-cystine supplied in the fresh medium. However, the cells continually import L-cystine from the medium and export L-cysteine. High levels of glutamic acid are believed to restrict this phenomenon, and there fore also influence the balance between L-cystine and L-cysteine. Accordingly, the preferred compositions comprise a high concentration of L-cystine and a low concentration of L-glutamic acid. For the purposes of the present invention, the L-cysteine and L-cystine are considered to be equivalent on a weight basis, because L-cysteine is rapidly converted to L-cystine by reaction with oxygen in the cell culture medium. L-cysteine also includes salts of L-cysteine or L-cystine, such as L-cystine dihydrochloride. L-glutamic acid includes salts of L-glutamic acid, and includes L-glutamate.

In an alternative embodiment, low levels of L-cystine and high levels of L-glutamic acid may be used. In this embodiment the concentration of L-cystine is preferably at or below about 0.4 mM, more preferably at or below about 0.2 mM, and the concentration of L-glutamic acid is preferably at least about 1.4 mM, more preferably at least about 2.7 mM glutamic acid.

In order to further promote the formation of dimers of BMPs or other proteins with increased stability, one can genetically engineer the DNA sequence encoding the protein to provide one or more additional cysteine residues to increase potential dimer formation. The resulting DNA sequence would be capable of producing a "cysteine added variant" of the protein. Alternatively, if desired, one could engineer the DNA sequence in order to delete one or more cysteine residues. Production of "cysteine added variants" of proteins is described in U.S. Pat. No. 5,166,322, the disclosure of which is hereby incorporated by reference. The use of cysteine added variants or cysteine depleted variants is within the present invention.

The following examples illustrate the invention with respect to one particular embodiment involving the production of recombinant human BMP-2. However, the examples are not limiting, and other modifications and variations are contemplated to be within the scope of the invention. In particular, with minor modifications and variations within the skill of the art, the present invention can be used for recombinant production of other proteins, particularly members of the TGF-β superfamily and BMP subfamily of proteins, as described above.

EXAMPLES

Different cystine/glutamic acid concentrations were tested in four 1-L bioreactors which $CO_2$ concentration was maintained at 7% by maitaining constant air/$CO_2$ overlay, pH was controlled at 7.0 by adding 2N titrant, and dissolved oxygen was controlled at 23% by sparging pure Oxygen. The bioreactors were kept at a temperature of 37° C. A Chinese Hamster Ovary [CHO] cell line, coexpressing BMP-2 and dihydrofolate reductase, was developed at Genetics Institute by transfection with a vector which contained BMP-2 cDNA. Cells were grown in bioreactors in fixed medium with variable cystine and glutamic acid concentrations as follows: 1) 1.4 mM cystine with 0.2 mM glutamic acid [high cystine, low glutamic acid]; 2) 0.2 mM cystine with 2.7 mM glutamic acid [low cystine, high glutamic acid]; 3) 0.2 mM cystine with 0.2 mM glutamic acid [low cystine, low glutamic acid]; and 4) 1.4 mM cystine with 2.7 mM glutamic acid [high cystine, high glutamic acid].

At all conditions, cells were suspended in each fresh media in 1-L bioreactors at the starting cell density of $0.37 \times 10^6$ cells/ml. After 72 hours, cell densities were determined. To test the medium effect on BMP-2 structures, 5 ml culture was withdrawn from each bioreactor. Cells were removed from the culture and the conditioned media were aliquated in 1 ml tubes and stored at $-80°$ C.

The principal assay used to investigate the different forms of BMP-2 in conditioned media is the SDS-PAGE ECL western. On SDS-PAGE, a molecular weight of approximately 30K represents the approximate location of desired BMP-2 mature form. There are also three bands with molecular weight of approximately 18K which are believed to represent dissociable dimer; the upper band is believed to be a cysteinylated dissociable dimer, the lower band is believed to be a free sulfhydryl dissociable dimer, and the middle band is believed to be a mixed of cysteinylated dissociable dimer and free sulfhydryl dissociable dimer.

Western Blot Analysis

In the Western Blot, we observed that the conditions of 1.2 mM cystine with 0.2 mM glutamic acid and 0.2 mM cystine with 2.7 mM glutamic acid have the least amount of dissociable dimer formation (correspondingly higher amount of desired BMP-2 dimer). Significantly higher amounts of dissociable dimer species have been found at the condition of 0.2 mM cystine with 0.2 mM glutamic acid [low cystine, low glutamic acid]. And most of the dissociable dimers are at the lower and middle location (corresponding to unstable free sulfhydryl dissociable dimer), with some upper band also observed. At the condition of 1.4 mM cystine with 2.7 mM glutamic acid [high cystine, high glutamic acid], a moderate amount of dissociable dimer was observed, and more prevalent dissociable dimer bands are at the top or middle location (cysteinylated dissociable dimer). These results are summarized in Table I. In the table, each [+] indicates a correspondingly higher amount of dissociable dimer present.

TABLE I

| Conditions | Upper band (Cysteinylated dissociable dimer) | Middle Band (Mixed dissociable dimer) | Lower Band (Free sulfhydryl dissociable dimer) |
|---|---|---|---|
| 0.2 Cys 0.2 Glu | + | ++++ | +++++ |
| 0.2 Cys 2.7 Glu | – | ++ | – |
| 1.4 Cys 0.2 Glu | – | + | – |
| 1.4 Cys 2.7 Glu | ++ | +++ | – |

What is claimed is:

1. A cell culture medium for the recombinant production of a disulfide bonded dimeric protein in mammalian Chinese Hamster Ovary (CHO) cells, said medium comprising L-cystine at a concentration of at least about 1.4 mM and L-glutamic acid at a concentration of at most about 0.2 mM.

2. A method for the recombinant production of a disulfide bonded dimeric protein comprising the steps of culturing a mammalian cell suitable for recombinant expression of said dimeric protein in the cell culture medium of claim 1.

3. The method according to claim 2, wherein said dimeric protein is a member of the TGF-β superfamily of proteins.

4. The method according to claim 2, wherein said dimeric protein is a member of the BMP subfamily of proteins.

5. The method according to claim 4, wherein said dimeric protein is selected from the group consisting of BMP-2, BMP-4, and BMP-7.

6. A method for recombinant production of a disulfide bonded dimeric protein of the TGF-β superfamily, comprising the step of culturing a mammalian cell suitable for recombinant expression of said dimeric protein in a cell culture medium comprising L-cystine at a concentration of at least about 1.4 mM, and L-glutamic acid at a concentration of at most about 0.2 mM.

7. The method of claim 6, wherein said dimeric protein is a member of the BMP superfamily of proteins.

8. The method of claim 7, wherein said dimeric protein is selected from the group consisting of BMP-2, BMP-4, and BMP-7.

9. A method for recombinant production of a BMP selected from BMP-2, BMP-4, or BMP-7, comprising the step of culturing a mammalian cell suitable for recombinant expression of said BMP in a cell culture medium comprising L-cystine at a concentration of about 1.4 mM and L-glutamic acid at a concentration of about 0.2 mM.

10. A method for culturing mammalian Chinese Hamster Ovary (CHO) cells which are suitable for recombinant expression of dimeric protein said method comprising culturing said cells in a cell culture medium comprising L-cystine at a concentration of at least about 1.4 mM and L-glutamic acid at a concentration of less than or equal to about 0.2 mM.

11. A method according to claim 10, wherein the dimeric protein is a member of the TGF-β superfamily of proteins.

12. A method according to claim 10, wherein the dimeric protein is a member of the BMP subfamily of proteins.

13. The method of claim 12, wherein the dimeric protein is selected from the group consisting of BMP-2, BMP-4 and BMP-7.

14. The method of claim 10, wherein the dimeric protein is a member of the BMP subfamily of proteins.

15. The method of claim 14, wherein the dimeric protein is selected from the group consisting of BMP-2, BMP-4 and BMP-7.

16. The medium of claim 1, wherein the concentration of said L-cystine is about 1.4 mM and the concentration of said L-glutamic acid is about 0.2 mM.

* * * * *